US010512648B2

(12) United States Patent
Ballestrero et al.

(10) Patent No.: US 10,512,648 B2
(45) Date of Patent: *Dec. 24, 2019

(54) TYROSINE KINASE INHIBITORS FOR USE IN A METHOD OF TREATING CANCER IN ASSOCIATION WITH A REDUCED CALORIC INTAKE

(71) Applicants: UNIVERSITÀ DEGLI STUDI DI GENOVA, Genoa (IT); L-NUTRA INC., Culver City, CA (US)

(72) Inventors: Alberto Ballestrero, Genoa (IT); Irene Caffa, Alassio (IT); Valter Longo, Culver City, CA (US); Alessio Nencioni, Genoa (IT); Patrizio Odetti, Genoa (IT); Franco Patrone, Genoa (IT)

(73) Assignees: UNIVERSITÀ DEGLI STUDI DI GENOVA, Genoa (IT); L-NUTRA INC., Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/158,544

(22) Filed: Oct. 12, 2018

(65) Prior Publication Data
US 2019/0105323 A1 Apr. 11, 2019

Related U.S. Application Data

(63) Continuation of application No. 15/129,569, filed as application No. PCT/EP2015/056918 on Mar. 30, 2015, now Pat. No. 10,117,872.

(30) Foreign Application Priority Data

Mar. 28, 2014 (IT) .............................. MI2014A0537

(51) Int. Cl.
| | | |
|---|---|---|
| *A61K 31/57* | (2006.01) | |
| *A61K 31/517* | (2006.01) | |
| *A61K 31/403* | (2006.01) | |
| *A61K 31/437* | (2006.01) | |
| *A61K 31/44* | (2006.01) | |
| *A61K 31/4439* | (2006.01) | |
| *A61K 31/47* | (2006.01) | |
| *A61K 31/496* | (2006.01) | |
| *A61K 31/506* | (2006.01) | |
| *A61K 31/519* | (2006.01) | |
| *A61K 31/5355* | (2006.01) | |
| *A61K 31/5365* | (2006.01) | |
| *A61K 31/4545* | (2006.01) | |

(52) U.S. Cl.
CPC .......... *A61K 31/517* (2013.01); *A61K 31/403* (2013.01); *A61K 31/437* (2013.01); *A61K 31/44* (2013.01); *A61K 31/4439* (2013.01); *A61K 31/4545* (2013.01); *A61K 31/47* (2013.01); *A61K 31/496* (2013.01); *A61K 31/506* (2013.01); *A61K 31/519* (2013.01); *A61K 31/5355* (2013.01); *A61K 31/5365* (2013.01)

(58) Field of Classification Search
CPC .................................................... A61K 31/517
USPC ...................................................... 514/266.24
See application file for complete search history.

(56) References Cited

U.S. PATENT DOCUMENTS

| | | | |
|---|---|---|---|
| 8,728,815 | B2 | 5/2014 | Longo |
| 10,117,872 | B2 * | 11/2018 | Ballestrero .......... A61K 31/403 |
| 2008/0166427 | A1 | 7/2008 | Nomura et al. |
| 2008/0242638 | A1 | 10/2008 | Longo |
| 2011/0118528 | A1 | 5/2011 | Longo |

OTHER PUBLICATIONS

Dhillon, Drugs (2018) 78:1133-1144).*
International Search Report (ISR) dated Jul. 24, 2015 in International (PCT) Application No. PCT/EP2015/056918.
Alessandro Laviano et al., "Toxicity in Chemotherapy—When Less is More", The New England Journal of Medicine, vol. 366, No. 24, pp. 2319-2320, Jun. 14, 2012, XP008172000, ISSN: 1533-4406, cited in the ISR.
Fernando M. Safdie et al., "Fasting and Cancer Treatment in Humans: A Case series report", vol. 1, No. 12, pp. 1-20, Dec. 2009, XP002729596, ISSN: 1945-4589, cited in the ISR.
Fernando Safdie et al., "Fasting Enhances the Response of Glioma to Chemo- and Radiotherapy", PLOS ONE, vol. 7, No. 9, E44603, pp. 1-9, Sep. 11, 2012, XP055139410, ISSN: 1932-6203, DOI: 10.1371/journal.pone/0044603, cited in the ISR.
EI Heath et al., "A Phase I Study of the Pharmacokinetic and Safety Profiles of Oral Pazopanib with a High-Fat or Low-Fat Meal in Patients with Advanced Solid Tumors", Clinical Pharmacology & Therapeutics, vol. 88, No. 6, pp. 818-823, Dec. 27, 2010, XP055139340, ISSN: 0009-9236, DOI: 10.1038/clpt.2010.199, cited in both the specification and ISR.

(Continued)

*Primary Examiner* — Nizal S Chandrakumar
(74) *Attorney, Agent, or Firm* — Wenderoth, Lind & Ponack, L.L.P.

(57) ABSTRACT

A tyrosine kinase inhibitor (TKI) for use in a method for the treatment of cancer in a patient, wherein the method comprises subjecting the patient to reduced caloric intake, i.e a daily caloric intake reduced by 10-100%, including starvation, for a period of 24-190 hours and administering the tyrosine kinase inhibitor to the patient during such period; the tyrosine kinase inhibitor is preferably selected among Lapatinib, Crizotinib, Gefitinib, Erlotinib, Afatinib and Regorafenib.

6 Claims, 4 Drawing Sheets

(56) References Cited

OTHER PUBLICATIONS

Bujko Jacek et al., "The effect of model diets with various fat and carbohydrate content on consumption of energy reserves during short-term starvation of laboratory animals", Database Biosis [Online] Biosciences Information Service, Philadelphia, PA, US, 1992, XP002742342, Database accession No. PREV1993950380815, & Polish Journal of Food and Nutrition Sciences, vol. 1, No. 3, pp. 109-117, 1992, ISSN: 1230-0322, cited in the ISR.
Sebastian Brandhorst et al., "Short-term calorie and protein restriction provide partial protection from chemotoxicity but do not delay glioma progression", Experimental Gerontology, vol. 48, No. 10, pp. 1120-1128, Feb. 21, 2013, XP028704571, ISSN: 0531-5565, DOI: 10.1016/J.EXGER.2013.02.016, cited in the ISR.
CANSA (Cancer Association of South Africa), CANSA Detectives, Novel Strategies in Chemotherapeutic Intervention, Nov. 2013.
Fung, Cancer Biology & Therapy 13:14, 1417-1424; Dec. 2012.
Alessandro, The New England Journal of Medicine, 2012, 366(24), 2319-2320, Health, Clinical Pharm.
Araki, Clinical Medicine Insights: Oncology (2012), 6, 407-421.
Heath, Clinical Pharmacology & Therapeutics, 2010, 88(6), 818-823.

* cited by examiner

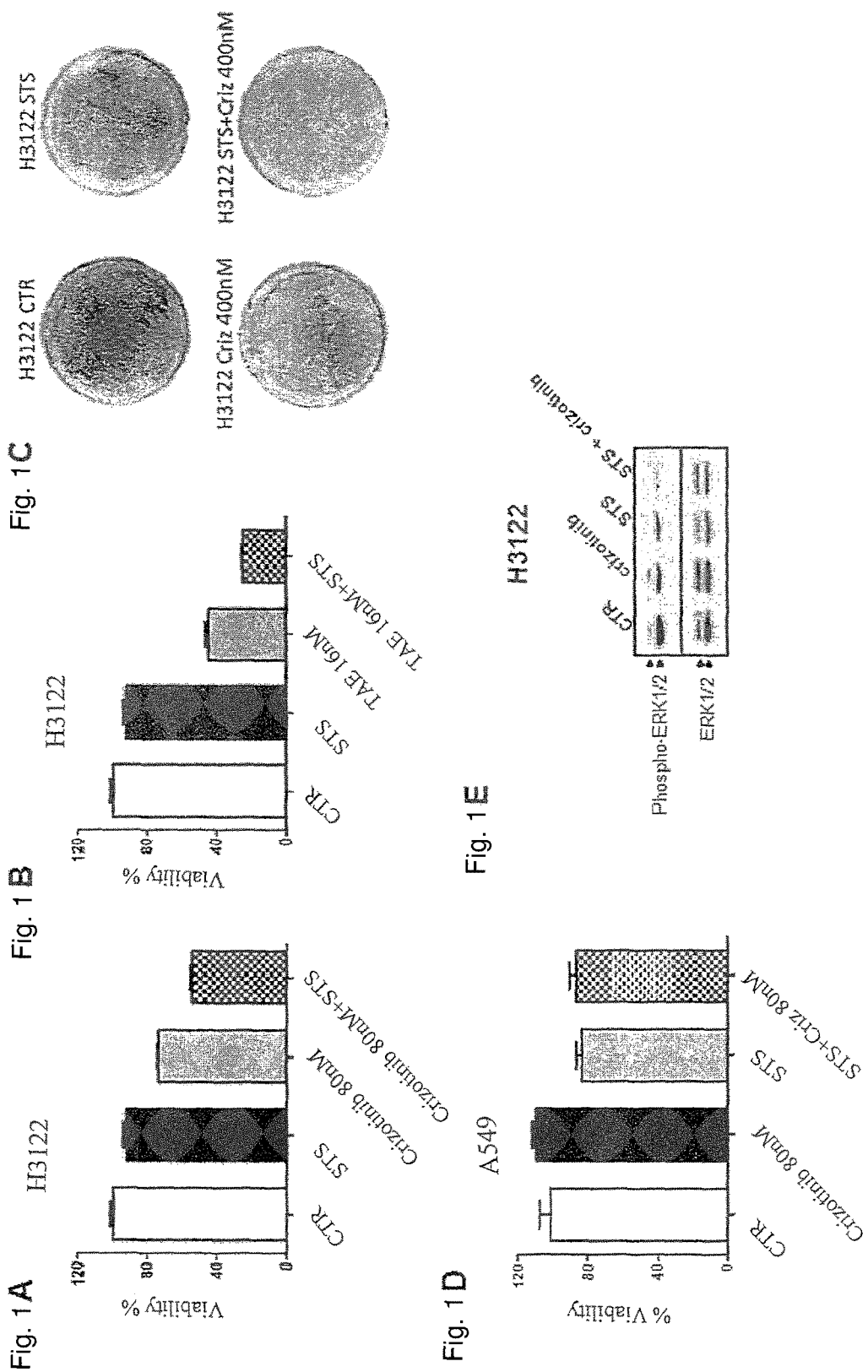

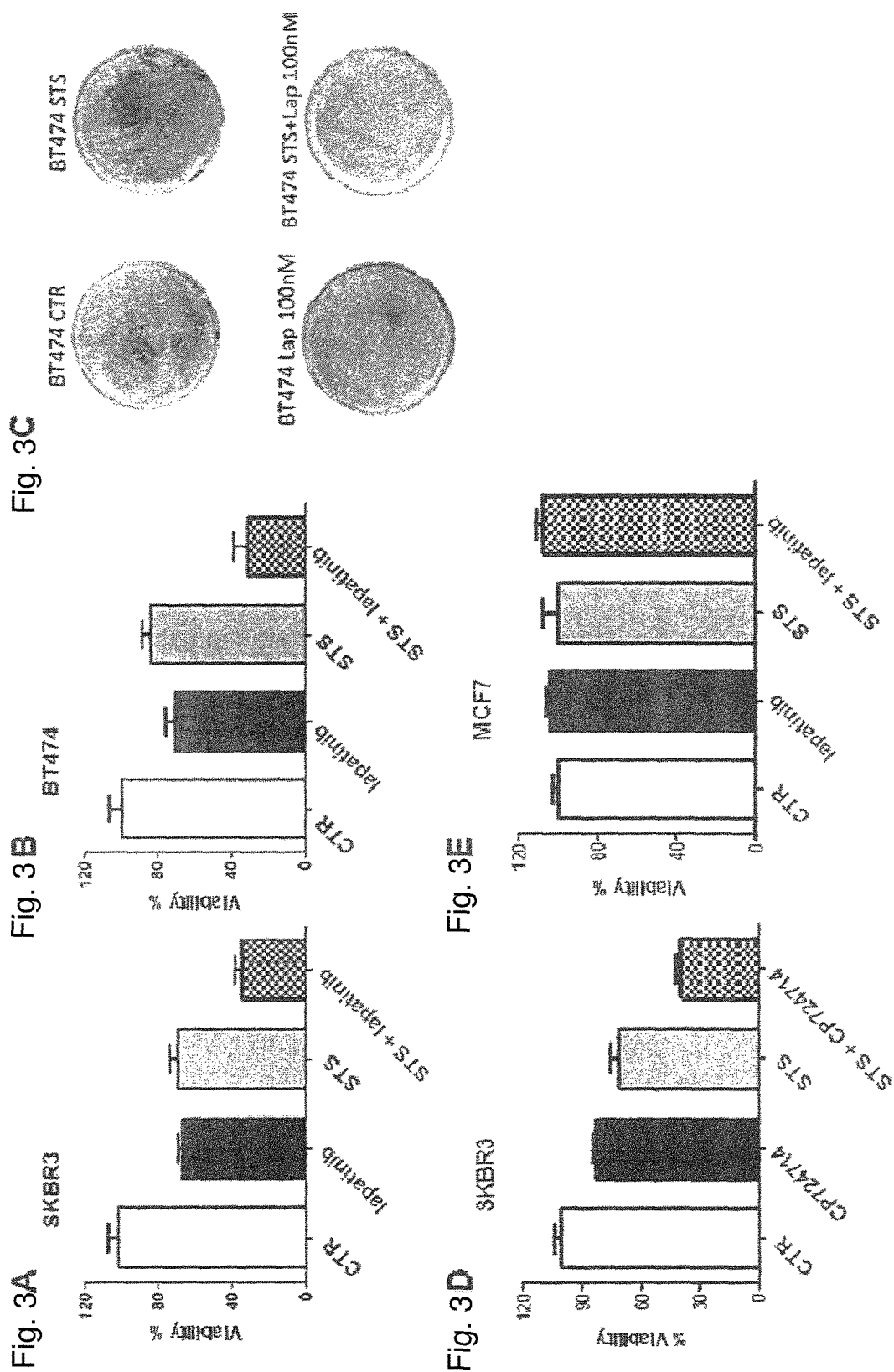

TYROSINE KINASE INHIBITORS FOR USE IN A METHOD OF TREATING CANCER IN ASSOCIATION WITH A REDUCED CALORIC INTAKE

TECHNICAL FIELD

The present invention concerns the technical field of the pharmaceutical industry.

In particular, the invention relates to compounds with tyrosine kinase inhibiting activity for use in the treatment of cancer in association with a defined dietetic regimen.

PRIOR ART

Molecularly targeted agents that interfere with the tyrosine kinase activity of their target are now the mainstay of treatment in several types of cancer in advanced stages. Gefitinib, erlotinib and afatinib (EGFR tyrosine kinase inhibitors—TKIs) have changed the natural history of advanced non-small cell lung cancer—NSCLC—with mutated EGFR with a proven superiority over standard platinum-based chemotherapy and objective response rates observed in 60-80% of the patients (1).

The anaplastic lymphoma kinase (ALK) inhibitor crizotinib is successfully employed in NSCLC with EML4-ALK translocations (2), while lapatinib (a dual HER2/EGFR TKI), and regorafenib (a multitarget TKI) are approved for treating HER2+ metastatic breast cancer (BC) and metastatic colorectal cancer (CRC), respectively (3-5).

Despite their success, a major limitation of these agents is that their efficacy is frequently short lived with the result that virtually all patients progress and ultimately succumb to their disease (1, 4, 5). Thus, strategies that help increase the efficacy of these agents making them more powerful and capable of more effectively eradicating cancer cells are warranted.

It is also known from a number of studies that short courses of starvation (short-term starvation, STS) sensitize cancer cells to DNA damaging agents, including chemotherapeutics and radiotherapy (6-8). This effect essentially reflects the inability of malignant cells to adapt to nutrient deprivation, primarily due to the aberrant activation of growth promoting signaling cascades. Vice versa, non-transformed tissues may even benefit from STS by reverting to a self-protection mode characterized by reduced cell growth, increased sirtuin activity, and autophagy activation, thus becoming more resistant to genotoxic stress and able to tolerate doses of chemotherapeutics that would otherwise be lethal for non-starved cells (9).

The discovery that STS increases the efficacy of chemotherapy in cancer cells, while at the same time shielding healthy cells from its toxicity, has recently attracted strong attention to this approach amongst physicians (10) and patients, and several pilot trials are currently exploring STS in combination with chemotherapy in humans (including studies performed at the University of Genoa, USC Norris Comprehensive Cancer Center, Mayo Clinic, and at the University of Leiden; NCT01304251, NCT01175837, NCT00936364, NCT01175837).

However, combining fasting (or reduced-calorie diets) with chemotherapy presents important limitations. In the first place, there is a strong concern among oncologists that adding starvation to debilitating therapies, such as chemotherapy or radiotherapy, might lead to unacceptable weight losses.

Second, chemotherapy and radiotherapy are frequently administered in combination with corticosteroids (to counter side effects, such as nausea, and allergic reactions) and this may prevent some of the metabolic adaptations to starvation (i.e. hypoglicemia) which are thought to underlie its beneficial effects in cancer patients. Thus, the benefits of fasting (or reduced-calorie diets) could be better exploited in combination with more modern anticancer agents, such as tyrosine kinase inhibitors, which have less side effects and act through mechanisms that are totally different from those which chemotherapeutics are based on.

Nevertheless, no reliable forecasts can be made on the effects that fasting (or reduced-calorie diets) may have on the efficacy of an anticancer therapy based on tyrosine kinase inhibitors.

For these reasons, the research carried out by the Applicant focused on the investigation of the possible interaction between starvation or reduced-calorie diets and an anticancer therapy based on tyrosine kinase inhibitors.

The present invention is the result of the above research activity.

E I Heath et al.: "A phase I study of the pharmacokinetic and safety profiles of oral pazopanib with a high-fat or low-fat meal in patients with advanced solid tumors", Clinical Pharmacology and Therapeutics, vol. 88, no. 6, 2012-12-27, pages 818-823, disclose the use of the TKI pazopanib for the treatment of advanced solid tumors. In this study, the authors concluded that pazopanib should be administered in the fasted state, at least 1 h before or 2 h after a meal, to minimize the within-day and between-day variability in systemic exposure to pazopanib that may be caused by the variability of food intake in patients with cancer. Nothing is said concerning a possible enhancement of the efficacy of the treatment with pazopanib obtained by subjecting the patients to a period of reduced caloric intake or starvation during such treatment.

US 2008/166427 discloses a method for potentiating the antitumor effect of the antimetabolite tegafur, while reducing gastrointestinal toxicity, which method comprises administering, together with tegafur, a dihydropyrimidine dehydrogenase inhibitor in an amount effective for potentiating the antitumor effect and an oxonic acid in an amount effective for suppressing gastrointestinal toxicity, under fasting conditions. Optionally, a chemotherapy agent can additionally be administered and such agent can be i.a. gefitinib, a TKI. A potentiating effect on the antitumor acitivity of tegafur in fasting conditions is only disclosed in connection with the dihydropyrimidine dehydrogenase inhibitor and not with gefitinib. The fasting conditions are defined as fasting at least one hour before a meal or after a meal and preferably 1-2 hours before or after a meal.

SUMMARY OF THE INVENTION

In an aspect thereof, the present invention relates to a tyrosine kinase inhibitor for use in a method for the treatment of cancer in a human patient, wherein the method comprises subjecting said patient to reduced caloric intake for a period of 24-190 hours while said patient is being treated with said tyrosine kinase inhibitor.

By reduced caloric intake it is hereby meant a daily caloric intake reduced by 10-100%, preferably by 50-100%, more preferably by 85-100%, with respect to the regular caloric intake, including total starvation.

The subject's regular caloric intake is the number of kcal that the subject consumes to maintain his/her weight. The subject's normal caloric intake may be estimated by interviewing the subject or by consideration of a subject's weight. As a rough guide, subject's normal caloric intake is on average 2600 kcal/day for men and 1850 kcal/day for women. Preferably, when the daily caloric intake is reduced by 10-85%, the patient is fed with foods with a high content of monounsaturated and polyunsaturated fats and a reduced content of proteins and carbohydrates 50% of calories coming from fat). This because a diet based on such foods has beneficial effects that are similar to those of starvation (16).

Preferably said period of reduced caloric intake ranges from 48 to 150 hours, and most preferably it is of about 120 hours.

The tyrosine kinase inhibitor (TKI) is preferably selected from the group consisting of Afatinib, Axitinib, Bosutinib, Crizotinib, Dasatinib, Erlotinib, Fostamatinib, Gefitinib, Imatinib, Lapatinib, Lenvatinib, Nilotinib, Pazopanib, Ruxolitinib, Regorafenib, Sorafenib, Sunitinib, SU6656, Tofacitinib, Vandetanib and Vemurafenib.

The most preferred tyrosine kinase inhibitors for the use according to the present invention are selected from the group consisting of Lapatinib, Crizotinib, Gefitinib, Erlotinib, Afatinib and Regorafenib.

As used herein, "cancer" refers to a disease or disorder characterized by uncontrolled division of cells and the ability of these cells to spread, either by direct growth into adjacent tissue through invasion, or by implantation into distant sites by metastasis. Examples of cancers include, but are not limited to, primary cancer, metastatic cancer, carcinoma, lymphoma, leukemia, sarcoma, mesothelioma, glioma, germinoma, choriocarcinoma, prostate cancer, lung cancer, breast cancer, colorectal cancer, gastrointestinal cancer, bladder cancer, pancreatic cancer, endometrial cancer, ovarian cancer, melanoma, brain cancer, testicular cancer, kidney cancer, skin cancer, thyroid cancer, head and neck cancer, liver cancer, esophageal cancer, gastric cancer, intestinal cancer, colon cancer, rectal cancer, myeloma, neuroblastoma, pheochromocytoma, and retinoblastoma.

Preferably, the cancer is lung cancer, colorectal cancer, kidney cancer, breast cancer, leukemia, thyroid cancer, lymphoma, pancreatic cancer, soft tissue sarcoma, gastrointestinal cancer, melanoma.

The above-mentioned period of reduced caloric intake with concurrent administration of the tyrosine kinase inhibitor to the patient can be repeated one or more times after respective periods of 5-60 days, during which the patient is given the tyrosine kinase inhibitor while following a diet involving a regular caloric intake.

The above-mentioned reduced calorie intake regimen preferably corresponds to less than 300 kcal/day, more preferably 100-200 Kcal/day.

Such reduced caloric intake can be obtained by means of dietetic foods with reduced caloric and protein content but containing all necessary micronutrients to prevent malnutrition.

In another aspect, the present invention relates to a pharmaceutical composition comprising a tyrosine kinase inhibitor as defined above and a pharmaceutically acceptable carrier for use in the method for the treatment of cancer in a patient as defined above.

In a further aspect, the present invention relates to a method of treating a cancer cell with a tyrosine kinase inhibitor, comprising:
cultivating a cancer cell in a medium with reduced serum or glucose concentration; and
treating the cancer cell with a tyrosine kinase inhibitor.

The serum concentration in the medium is preferably reduced by 10-90% and the glucose concentration in the medium is preferably reduced by 20-90%.

As it will become clear from the experimental results reported in the following sections, it has unexpectedly been found that starvation, in particular STS, and also a reduced caloric intake for periods of 24-72, positively affect the efficacy of a concurrent anticancer treatment with a tyrosine kinase inhibitor.

A positive effect on the efficacy of a concurrent anticancer treatment with a TKI is also obtained when the above mentioned periods of reduced caloric intake are replaced by corresponding periods of regular caloric intake, during which the patients are only fed with the above-mentioned foods with a high content of monounsaturated and polyunsaturated fats and a reduced content of proteins and carbohydrates 50% of calories coming from fat), since a diet based on such foods has beneficial effects that are similar to those of starvation (16).

In an aspect thereof, the present invention thus also concerns a tyrosine kinase inhibitor for use in a method for the treatment of cancer in a human patient, wherein the method comprises feeding said patient only with foods with a high content of monounsaturated and polyunsaturated fats and a reduced content of proteins and carbohydrates 50% of calories coming from fat), in such an amount as to ensure a regular daily caloric intake, for a period of 24-190 hours, while said patients is being treated with said tyrosine kinase inhibitor.

Differently from what happened with the previously known treatments associating STS with chemotherapy or radiotherapy, which generally required the administration of a corticosteroid in order to counter the side effects (i.e. nausea) and allergic reactions caused by chemotherapy and radiotherapy, the method according to the present invention does not require the administration of corticosteroids, because tyrosine kinase inhibitors do not display the severe side effects of chemotherapy or radiotherapy.

This is quite a significant advantage over the above-mentioned known treatments, because the metabolic adaptations to starving (e.g. hypoglycemia), which are beneficial in terms of response by the tumor cells, are not prevented or hindered by a concomitant administration of corticosteroids.

The compounds and compositions according to the invention may be administered with any available and efficient delivery system, comprising, but not limited to, oral, buccal, parenteral, inhalatory routes, topical application, by injection, by transdermic or rectal route (for ex. by means of suppositories) in dosage unit formulations containing conventional, pharmaceutically acceptable and non-toxic carriers, adjuvants and vehicles. The administration by parenteral route comprises subcutaneous, intravenous, intramuscular, intrasternal injection or infusion techniques.

The solid dosage forms for the administration by oral route comprise, for example, capsules, tablets, powders, granules and gels. In such solid dosage forms, the active compound may be mixed with at least one inert diluent such as, for example, sucrose, lactose or starch. These dosage forms normally also comprise additional substances different from the inert diluents, such as, for example, lubricating agents like magnesium stearate.

The injectable preparations, for example aqueous or oily sterile injectable solutions or suspensions, may be formulated according to the known technique and by optionally using appropriate dispersing, wetting and/or suspending agents.

The pharmaceutical preparations according to the present invention may be produced by using conventional pharmaceutical techniques, as described in the various pharmacopoeias or handbooks of the field such as, for example, "Remington's Pharmaceutical Sciences Handbook", Mack Publishing, New York, 18th Ed., 1990.

The average daily dosage of the compounds according to the present invention depends on many factors, such as, for example, the seriousness of the disease and the conditions of the patient (age, weight, sex): The dose may generally vary from 1 mg to 1500 mg per day of compound according to the invention, optionally divided into more administrations.

The present invention will be further described with reference to the appended drawings and to certain embodiments, which are provided here below by way of illustration and not of limitation.

BRIEF DESCRIPTION OF THE DRAWINGS

FIG. 1A is a bar graph showing the respective effects of short term starvation (STS), Crizotinib and STS+Crizotinib on the viability of H3122 non-small cell lung cancer cells (NSCLC).

FIG. 1B is a bar graph showing the respective effects of short term starvation (STS), TAE684 and STS+TAE684 on the viability of H3122 NSCLC cells.

FIG. 1C is a photograph showing the effects of short term starvation (STS), Crizotinib and STS+Crizotinib on H3122 (NSCLC) cells plated in Petri dishes in DMEM medium.

FIG. 1D is a histogram showing the respective effects of short term starvation (STS), Crizotinib and STS+Crizotinib on the viability of A549 NSCLC cells (which do not harbor an EML4-ALK translocation and, therefore, are normally insensitive to crizotinib).

FIG. 1E is an immunoblotting showing the levels of phospho-ERK and total ERK in cell lysates from H3122 cells subjected to, respectively, STS, treatment with Crizotinib and STS+treatment with Crizotinib.

FIG. 3A is a histogram showing the respective effects of short term starvation (STS), Lapatinib and STS+Lapatinib on the viability of SKBR3 cells (HER2+ breast cancer).

FIG. 3B is a histogram showing the respective effects of short term starvation (STS), Lapatinib and STS+Lapatinib on the viability of BT474 cells (HER2+ breast cancer).

FIG. 3C is a photograph showing the effects of short term starvation (STS), Lapatinib and STS+Lapatinib on BT474 cells plated in Petri dishes in DMEM medium.

FIG. 3D is a histogram showing the respective effects of short term starvation (STS), CP724714 (an HER tyrosine kinase inhibitor) and STS+CP724714 on the viability of SKBR3 cells.

FIG. 3E is a histogram showing the respective effects of short term starvation (STS), Lapatinib and STS+Lapatinib on MCF7 cells (which do not harbor a HER2 amplification and, therefore, are normally insensitive to lapatinib).

DETAILED DESCRIPTION

Figure 2A:
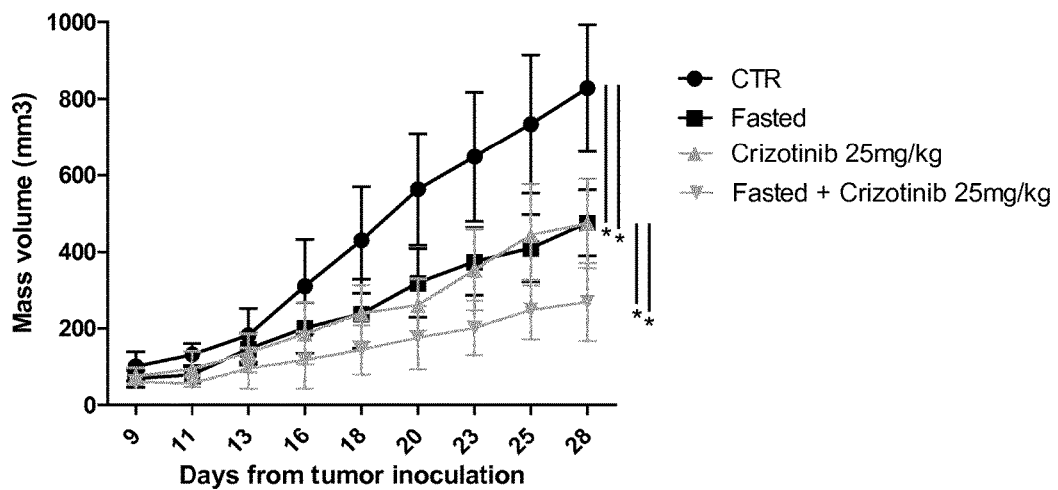
FIG. 2A is a diagram showing the size (mass volume) of H3122 xenografts in mice subjected to, respectively, STS; Crizotinib treatment; STS+Crizotinib treatment; no treatment (control). *p<0.05.

The Applicants performed several experiments to assess whether conditions that mimic the metabolic effects of starvation in vitro (cell culture in the presence of low serum (1% FBS) and low glucose (0.5 g/L) sensitize cancer cells to two TKIs, Crizotinib and Lapatinib, that are commonly used in EML4-ALK+NSCLC and in HER2+ BC (breast cancer cells), respectively.

With reference to FIGS. 1A and 1B, $3 \times 10^3$ H3122 cells were plated in 96 well plates in regular DMEM medium containing 10% FBS. 24 h later, the cell medium was removed and cells were incubated for 24 h either in the same medium (CTR) or in low-glucose (0.5 g/L) DMEM medium containing 1% FBS (STS). 24 h later cells were treated or not with the indicated concentrations of Crizotinib or TAE382 (TAE). 72 h later, viability was measured with sulforodhamine B-based assays.

With reference to FIG. 1C, $10^5$ H3122 cells were plated in 60 mm Petri dishes in regular DMEM medium. 24 h later, the cell medium was removed and cells were incubated for 24 h either in regular medium (CTR) or in STS conditions. 24 h later 400 nM Crizotinib was added (or not) to the cells. 5 days later, the cell medium was removed and the cells were cultured for two additional days in regular DMEM medium. 48 h later, the plates were stained with sulforodhamine B and photographed.

With reference to FIG. 1D, $3 \times 10^3$ A549 cells were plated in 96 well plates and treated with Crizotinib in the presence or absence of STS, as in the experiments of FIGS. 1A and 1B, before viability was measured in sulforodhamine B-based assays.

With reference to FIG. 1E, $10^5$ H3122 cells were plated in 6 well plates in regular DMEM medium containing 10% FBS. 24 h later, the cell medium was removed and cells were incubated for 24 h either in the same medium (CTR) or in low-glucose (0.5 g/L) DMEM containing 1% FBS (STS). 24 h later cells were treated or not with 400 nM Crizotinib. After 24 h, cell were used for cell lysate preparation and phospho-ERK (Thr202/Tyr204), and total ERK levels were detected by immunoblotting.

Having regard to the above experiments, it can be concluded that in H3122 NSCLC cells (which carry the EML4-ALK translocation), STS conditions strongly potentiated the activity of Crizotinib and of TAE684, an unrelated ALK inhibitor (FIG. 1A-C), leading to a virtual complete killing of NSCLC cells in the presence of 400 nM Crizotinib (FIG. 1C). Notably, A549 NSCLC cells, which do not have an EML4-ALK translocation, were insensitive to Crizotinib and STS did not increase the activity of the TKI in this cell line (FIG. 1D). Thus, STS did not simply increase the cytotoxic activity of Crizotinib, but instead it allowed to retain its specificity for cancer cells with aberrant ALK activity. Notably when administered to starved cells, Crizotinib was more effective at blocking signaling through the MAPK pathway (ERK1/2 phosphorylation) than it was in cells cultured in standard conditions (FIG. 1E), which suggests a plausible mechanism for the observed potentiation of Crizotinib efficacy through STS.

In line with this hypothesis is the observation that H3122 cells engineered to overexpress HRAS or HRAS V12 were resistant to crizotinib, STS-mimicking conditions or their combination (not shown), which is consistent with inhibition of the MAPK pathway playing a key role in the anticancer activity of these treatments.

With reference to FIG. 2A, six- to eight-week-old BALB/c athymic mice (nu+/nu+) were injected s.c. with $5\times10^6$ H3122 cells. When tumors became palpable, mouse were randomly assigned to one of four arms (six mice per treatment arm): control—normal diet (—); Crizotinib—normal diet with 3 cycles of Crizotinib (25 mg/kg/day via oral gavage for 5 days a week, Mon-Fri); STS [fasting (water only) for 48 h (Sun-Tue) for three cycles at 1-week intervals]; STS+Crizotinib. Tumor size was measured daily and tumor volume was calculated using the formula: tumor volume=$(w^2\times W)\times\pi/6$, where "w" and "W" are "minor side" and "major side" (in mm), respectively. At the end of treatment, mice were euthanized and tumor masses were excised and weighted (see FIG. 2B). Mouse weight was also monitored daily.

Figure 2B:
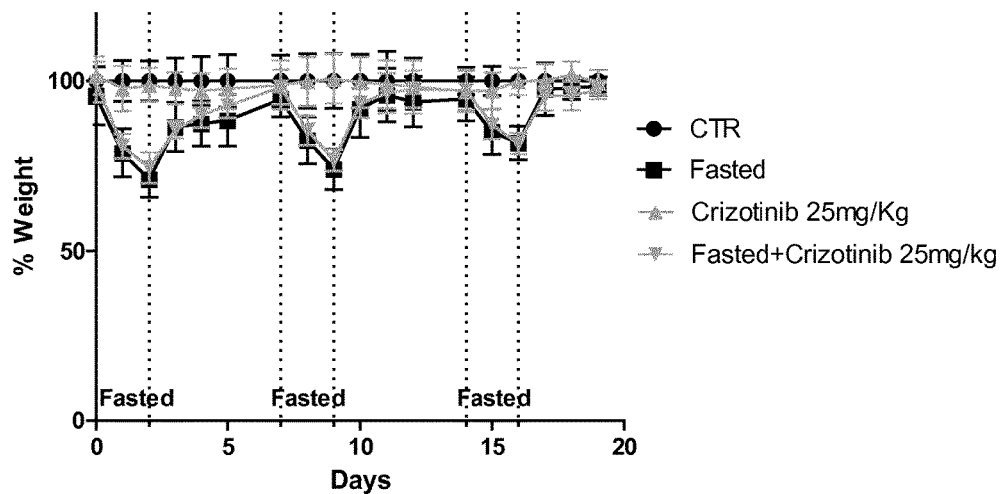
FIG. 2B is a diagram showing the body weight of mice subjected to, respectively, STS; Crizotinib treatment; STS+Crizotinib treatment; no treatment (control).

From the above reported experiments it can be observed that, in vivo, both fasting cycles and Crizotinib effectively reduced the growth of H3122 xenografts with no difference in terms of efficacy between the two approaches, but the combination Crizotinib+fasting was more active than either type of treatment alone (*: $p<0.05$; : $p<0.01$; *: $p<0.001$; FIG. 2A-B). Fasted mice exhibited transient weight losses, but fully recovered their weight between one cycle and the next (FIG. 2B). Clearly, this data indicates the potential of STS conditions to make ALK inhibitors more effective with possible strong benefits for the patients.

With reference to FIGS. 3A and 3B, $3\times10^3$ SKBR3 (FIG. 3A) or BT474 (FIG. 3B) cells/well were plated in 96 well plates in regular DMEM medium containing 10% FBS and 2.5 g/L glucose. 24 h later, the cell medium was removed and cells were incubated for 24 h either in the same medium (CTR) or in low-glucose (0.5 g/L) DMEM medium containing 1% FBS (STS). 24 h later cells were treated or not with 100 nM Lapatinib. 72 h later, viability was measured in sulforodhamine B-based assays.

With reference to FIG. 3C, $4\times10^5$ BT474 cells were plated in 60 mm Petri dishes in regular DMEM medium. 24 h later, the cell medium was removed and cells were incubated for 24 h either in regular medium (CTR) or in STS conditions. 24 h later 100 nM Lapatinib was added (or not) to the cells. 5 days later, the cell medium was removed and the cells were cultured for additional two days in regular DMEM medium. 48 h later, the plates were stained with sulforodhamine B and photographed.

With reference to FIGS. 3D and 3E, BT474 or MCF7 cells were plated as detailed with regard to FIGS. 3A and 3B, treated with 100 nM CP724714 (FIG. 3D) or Lapatinib (FIG. 3E) with or without STS conditions as detailed with respect to FIGS. 3A and 3B before viability was detected.

Figure 4:
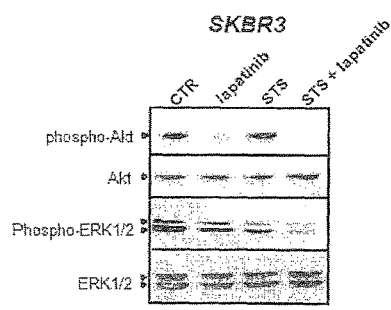
FIG. 4A is an immunoblotting showing the levels of phosphor-Akt, total Akt, phospho-ERK and total ERK in cell lysates from SKBR3 cells subjected to, respectively, STS, treatment with Lapatinib and STS+treatment with Lapatinib.
FIG. 4B is an immunoblotting showing the levels of phosphor-Akt, total Akt, phospho-ERK and total ERK in cell lysates from BT474 cells subjected to, respectively, STS, treatment with Lapatinib and STS+treatment with Lapatinib.
FIG. 4C is a flow cytometry analysis (forward scatter, FSC; 10,000 events per cell sample) of BT474 subjected to, respectively, STS, treatment with Lapatinib and STS+treatment with Lapatinib.
Figure 4:
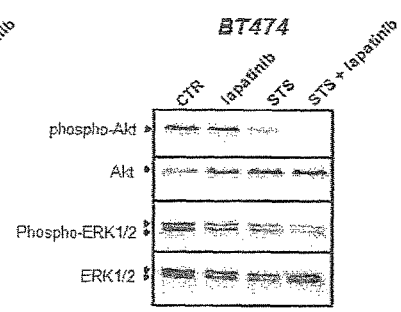
Figure 4:
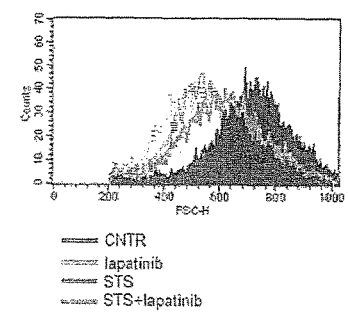

With reference to FIGS. 4A-C, $10^5$ SKBR3 (FIG. 4A) or BT474 (FIG. 4B) cells were plated in 6 well plates in regular DMEM medium containing 10% FBS. 24 h later, the cell medium was removed and cells were incubated for 24 h either in the same medium (CTR) or in low-glucose (0.5 g/L) DMEM medium containing 1% FBS (STS). 24 h later cells were treated or not with 100 nM Lapatinib. After 24 h, cell were either used for cell lysate preparation or for flow cytometry assays. Cell lysates were used for phospho-AKT (Ser473), total AKT, phospho-ERK (Thr202/Tyr204), and total ERK level detection by immunoblotting (FIGS. 4A and 4B). Flow cytometry (with a FACS Calibur, BD) was used to estimate cell size (FSC) by acquiring 10,000 events per cell sample (FIG. 4C).

From the experiments of FIGS. 3A-E, it can be noted that, in the case of Lapatinib, as shown in FIGS. 3A and 3B, both BT474 and SKBR3 (HER2+BC cell lines) cells were strongly sensitized to therapeutic concentrations of this agent by STS conditions (see also FIG. 3C).

Similar results were obtained using an unrelated HER2 TK inhibitor, CP724714 (13) (FIG. 3D), thus confirming that the observed cooperation between STS and Lapatinib was due to inhibition of HER2 TK activity. As expected (12, 14), MCF7 cells (FIG. 3E), which do not harbor HER2 amplification, were insensitive to Lapatinib and STS failed to enhance the activity of this TKI in this cell line, again indicating that STS-mimicking conditions potentiate the TKI activity without compromising its specificity. At the molecular level, cells treated with Lapatinib in STS-mimicking conditions exhibited a more pronounced inhibition of AKT and ERK1/2 signaling than cells treated with Lapatinib alone. Given the importance of these signaling cascades in the survival of HER2+BC (15), these findings could well justify the observed cooperation between the two types of interventions (FIG. 4A, B).

REFERENCES

1. Gridelli C, de Marinis F, Cappuzzo F, Di Maio M, Hirsch F R, Mok T, et al. Treatment of Advanced Non-Small-Cell Lung Cancer With Epidermal Growth Factor Receptor (EGFR) Mutation or ALK Gene Rearrangement: Results of an International Expert Panel Meeting of the Italian Association of Thoracic Oncology. Clinical lung cancer. 2013.
2. Gridelli C, Solange P, Sgambato A, Casaluce F, Adjei A A, Ciardiello F. ALK inhibitors in the treatment of advanced NSCLC. Cancer Treat Rev. 2013.
3. Geyer C E, Forster J, Lindquist D, Chan S, Romieu C G, Pienkowski T, et al. Lapatinib plus capecitabine for HER2-positive advanced breast cancer. N Engl J Med. 2006; 355:2733-43.
4. Gradishar W J. Emerging approaches for treating HER2-positive metastatic breast cancer beyond trastuzumab. Ann Oncol. 2013.
5. Carter N J. Regorafenib: a review of its use in previously treated patients with progressive metastatic colorectal cancer. Drugs & aging. 2014; 31:67-78.
6. Lee C, Raffaghello L, Brandhorst S, Safdie F M, Bianchi G, Martin-Montalvo A, et al. Fasting cycles retard growth of tumors and sensitize a range of cancer cell types to chemotherapy. Sci Transl Med. 2012; 4:124ra27.
7. Safdie F, Brandhorst S, Wei M, Wang W, Lee C, Hwang S, et al. Fasting enhances the response of glioma to chemo- and radiotherapy. PloS one. 2012; 7:e44603.
8. Shi Y, Felley-Bosco E, Marti T M, Orlowski K, Pruschy M, Stahel R A. Starvation-induced activation of ATM/Chk2/p53 signaling sensitizes cancer cells to cisplatin. BMC Cancer. 2012; 12:571.
9. Raffaghello L, Lee C, Safdie F M, Wei M, Madia F, Bianchi G, et al. Starvation-dependent differential stress resistance protects normal but not cancer cells against high-dose chemotherapy. Proc Natl Acad Sci USA. 2008; 105:8215-20.
10. Laviano A, Rossi Fanelli F. Toxicity in chemotherapy—when less is more. N Engl J Med. 2012; 366:2319-20.

11. Safdie F M, Dorff T, Quinn D, Fontana L, Wei M, Lee C, et al. Fasting and cancer treatment in humans: A case series report. Aging (Albany N.Y.). 2009; 1:988-1007.
12. Nencioni A, Cea M, Garuti A, Passalacqua M, Raffaghello L, Soncini D, et al. Grb7 upregulation is a molecular adaptation to HER2 signaling inhibition due to removal of Akt-mediated gene repression. PloS one. 2010; 5:e9024.
13. Munster P N, Britten C D, Mita M, Gelmon K, Minton S E, Moulder S, et al. First study of the safety, tolerability, and pharmacokinetics of CP-724,714 in patients with advanced malignant solid HER2-expressing tumors. Clinical cancer research: an official journal of the American Association for Cancer Research. 2007; 13:1238-45.
14. Konecny G E, Pegram M D, Venkatesan N, Finn R, Yang G, Rahmeh M, et al. Activity of the dual kinase inhibitor lapatinib (GW572016) against HER-2-overexpressing and trastuzumab-treated breast cancer cells. Cancer Res. 2006; 66:1630-9.
15. Rexer B N, Arteaga C L. Optimal targeting of HER2-PI3K signaling in breast cancer: mechanistic insights and clinical implications. Cancer Res. 2013; 73:3817-20.
16. Brandhorst S, Wei M, Hwang S, Morgan T E, Longo V D.

Short-term calorie and protein restriction provide partial protection from chemotoxicity but do not delay glioma progression. Exp Gerontol. 2013 Oct; 48(10):1120-8. doi: 10.1016/j.exger.2013.02.016. Epub 2013 Feb. 21.

The invention claimed is:

1. A method for treating a human patient affected by non-small cell lung cancer or colorectal cancer, said method comprising subjecting the patient to reduced caloric intake for a period of 24-190 hours, while the patient is being treated with a tyrosine kinase inhibitor (TKI), wherein:
when the patient is affected by non-small cell lung cancer, the TKI is Erlotinib or Gefitinib, when the patient is affected by colorectal cancer, the TKI is Regorafenib, and the reduced caloric intake corresponds to less than 300 kcal/day.

2. The method according to claim 1, wherein said period of reduced caloric intake is 48 to 150 hours.

3. The method according to claim 1, wherein said period of reduced caloric intake is about 120 hours.

4. The method according to claim 1, wherein said period of reduced caloric intake with concurrent administration of the tyrosine kinase inhibitor to the patient is repeated one or more times after respective periods of 5-60 days, during which said patient is given the tyrosine kinase inhibitor while following a diet involving a regular caloric intake.

5. The method according to claim 1, wherein said reduced caloric intake corresponds to 100-200 Kcal/day.

6. The method according to claim 1, wherein said reduced caloric intake is obtained by fasting or by means of dietetic food with reduced caloric and/or protein content but containing all necessary micronutrients to prevent malnutrition.

* * * * *